United States Patent
Kamiyama et al.

(10) Patent No.: US 8,389,001 B2
(45) Date of Patent: Mar. 5, 2013

(54) PRECURSOR COMPOSITION FOR CROSSLINKABLE PRESSURE-SENSITIVE ADHESIVE FOR SKIN

(75) Inventors: Fumio Kamiyama, Otokuni (JP); Ying Shu Quan, Kyoto (JP); Naohisa Kawamura, Kasukabe (JP); Hidenori Sawada, Kasukabe (JP)

(73) Assignee: Nipro Patch Co., Ltd., Saitama-ken (JP)

( * ) Notice: Subject to any disclaimer, the term of this patent is extended or adjusted under 35 U.S.C. 154(b) by 328 days.

(21) Appl. No.: 12/592,348

(22) Filed: Nov. 24, 2009

(65) Prior Publication Data

US 2010/0076112 A1    Mar. 25, 2010

Related U.S. Application Data

(62) Division of application No. 10/593,242, filed as application No. PCT/JP2005/007058 on Apr. 12, 2005, now abandoned.

(30) Foreign Application Priority Data

Apr. 13, 2004   (JP) .................. 2004-147022

(51) Int. Cl.
  *A61F 13/02*   (2006.01)
  *A61K 9/70*    (2006.01)
  *A61K 47/30*   (2006.01)
  *A61L 24/06*   (2006.01)
  *C08F 18/02*   (2006.01)

(52) U.S. Cl. .............. 424/448; 424/443; 514/772.1; 525/540; 526/319

(58) Field of Classification Search .......... None
See application file for complete search history.

(56) References Cited

U.S. PATENT DOCUMENTS

| | | | |
|---|---|---|---|
| 6,617,389 B1 | 9/2003 | Delaunoit et al. | 524/555 |
| 6,669,953 B1 | 12/2003 | Kamiyama | 424/449 |
| 2003/0113365 A1* | 6/2003 | Schaberg et al. | 424/449 |
| 2006/0110433 A1 | 5/2006 | Terahara et al. | 424/448 |

FOREIGN PATENT DOCUMENTS

| | | | |
|---|---|---|---|
| JP | 61-000010 | | 1/1986 |
| JP | 61-100520 | | 5/1986 |
| JP | 03-220120 | | 9/1991 |
| JP | 06-023029 | | 2/1994 |
| JP | 08-034964 | | 2/1996 |
| JP | 2002-535475 | | 10/2002 |
| JP | 2004-83520 | * | 3/2004 |
| WO | WO 00/44846 | | 8/2000 |
| WO | WO 02/09676 | | 2/2002 |
| WO | WO 02/069942 | | 9/2002 |
| WO | WO 00/44846 | * | 8/2003 |

OTHER PUBLICATIONS

International Search Report based on PCT/JP2005/007058 dated Jul. 25, 2005.
Supplementary European Search Report from Application No. EP 05 73 0606 dated Jul. 13, 2011.

* cited by examiner

*Primary Examiner* — Kevin S Orwig
(74) *Attorney, Agent, or Firm* — Roylance, Abrams, Berdo & Goodman, L.L.P.

(57) ABSTRACT

A composition for production of a crosslinkable pressure-sensitive adhesive for skin, obtained by dissolving in a solvent 100 parts by weight of an acrylic copolymer (copolymer A) comprising a (meth)acrylic acid alkyl ester as the main constituent component and 3-45 wt % diacetoneacrylamide as an essential constituent component, and containing no free carboxyl groups, and 0.1-30 parts by weight of an acrylic copolymer (copolymer B) comprising a (meth)acrylic acid alkyl ester as the main constituent component and a primary amino group and/or carboxyhydrazide group on a side chain, and containing no free carboxyl groups.

6 Claims, 1 Drawing Sheet

PRECURSOR COMPOSITION FOR CROSSLINKABLE PRESSURE-SENSITIVE ADHESIVE FOR SKIN

CROSS-REFERENCED APPLICATIONS

This is a Divisional Application of U.S. patent application Ser. No. 10/593,242, filed on Sep. 19, 2006, now abandoned and also claims the benefit of and priority to PCT/JP2005/007058, filed on Apr. 12, 2005, and Japanese Patent Application No. 2004-147022, filed on Apr. 13, 2004, the entire contents of which are incorporated herein by reference.

BACKGROUND

1. Technical Field

The present invention relates to a crosslinkable pressure-sensitive adhesive for skin, to a crosslinkable pressure-sensitive adhesive sheet for skin employing it, to a composition for production of the crosslinkable pressure-sensitive adhesive for skin and to a process for production of the crosslinkable pressure-sensitive adhesive for skin.

2. Background Art

Pressure-sensitive adhesive sheets for skin, in general, must reliably adhere for about 24 hours after being attached to skin and must also adhere without peeling during perspiration and bathing. Also for removal, they must be peelable with a degree of force that does not cause pain, and if the adhesion is stronger than necessary it can result in plucking of hairs and peeling of the corneum, as well as mechanical skin irritation by pulling of the skin. Consequently, this creates erythema that may persist for several days even after peeling, and therefore it is necessary to minimize this inconvenience. Moreover, it is important that no pressure-sensitive adhesive remain on the skin surface after the pressure-sensitive adhesive sheet has been removed from the skin.

Crosslinking of acrylic pressure-sensitive adhesives has been commonly employed in the prior art in pressure-sensitive adhesives for skin in order to improve cohesion of the pressure-sensitive adhesives. Such crosslinking is achieved almost entirely by using the acrylic acid in an acrylic copolymer, but its drawbacks include the facts that (1) the adhesion is excessively strong or chemical activity of the acrylic acid causes significant skin irritation, (2) in percutaneous absorption preparations containing drugs, the acrylic acid and basic drug interact and impede migration of the drug from the pressure-sensitive adhesive into the skin, thereby reducing the percutaneous absorption, and (3) polyisocyanate used as the crosslinking agent is highly active and often reacts with drugs, thereby impairing drug stability.

In Japanese Patent Laid-open (Kokai) Publication SHO No. 61-100520 there is proposed an acrylic acid-free pre-crosslinked pressure-sensitive adhesive, which comprises 45 mol % 2-ethylhexyl acrylate, 20-55 mol % vinylpyrrolidone and no greater than 35 mol % of an acrylic acid ester with 3-12 carbon atoms in the ester portion, as well as 0.005-0.5 wt % of a polyfunctional monomer with respect to the weight of the entire monomer. However, while percutaneous absorption preparations using this type of pressure-sensitive adhesive have satisfactory drug percutaneous absorption and stability, the cohesive strength is insufficient when softening agents and plasticizers are added to improve the drug release property, and therefore adhesive residue remains on the skin after the percutaneous absorption preparation is removed. Thus, the problem of adhesive residue must be solved in order to obtain excellent pressure-sensitive adhesive sheets for skin.

As modifications to crosslinking acrylic-based pressure-sensitive adhesives there have been proposed methods of obtaining pressure-sensitive adhesive sheets by crosslinking after coating and drying acrylic copolymer composition solutions containing large amounts of plasticizers, and specifically there may be mentioned Japanese Patent Publication No. 2700835 and Japanese Patent Publication No. 3014188. With such percutaneous absorption preparations, however, it is possible to increase the shape retention of the pressure-sensitive adhesive layer but difficult to design a preparation with balance between adhesion on the skin and cohesive force of the pressure-sensitive adhesive.

On the other hand, Japanese Patent Laid-open (Kohyo) Publication No. 2002-535475 proposes a method wherein an acrylic-based pressure-sensitive adhesive containing diacetoneacrylamide, and a plasticizer, are mixed with a polyamine such as adipic acid dihydrazide or hexanediamine, the mixture is coated and then the solvent is heated and dried for crosslinking.

However, the drawbacks of this method are the following: (1) Mixture of the low-molecular polyamine such as adipic acid dihydrazide or hexanediamine with the pressure-sensitive adhesive solution results in a coating mixture that gels within several hours and becomes impossible to coat.

(2) Low molecular polyamines such as adipic acid dihydrazide and hexanediamine crosslink the diacetoneacrylamide-containing acrylic-based pressure-sensitive adhesive when no drug is present, but in the presence of a drug they react therewith or the drug often interferes, thereby preventing crosslinking.

(3) Adipic acid dihydrazide has low organic solvent solubility, and therefore must be used as a solution in water for addition to the coating solution. Consequently, its use in a large amount promotes precipitation of polymers and renders handling inconvenient.

(4) Hydrazine compounds such as adipic acid dihydrazide are absorbed through the skin and are indicated as a toxicity risk, for which reason they have been unsuitable as additives for pressure-sensitive adhesives on skin.

SUMMARY

A crosslinkable pressure-sensitive adhesive for skin having satisfactory adhesive and release properties for human skin and low irritation against skin, as well as a crosslinkable pressure-sensitive adhesive for skin that is suitable for medical or cosmetic use, and it is another object of the invention to provide a composition for production of a crosslinkable pressure-sensitive adhesive for skin with excellent shelf life, which is suitable for production of the aforementioned crosslinkable pressure-sensitive adhesive for skin.

The crosslinkable pressure-sensitive adhesive for skin of the invention is formed by 100 parts by weight of an acrylic copolymer (copolymer A) comprising a (meth)acrylic acid alkyl ester as the main constituent component and 3-45 wt % diacetoneacrylamide as an essential constituent component, and containing no free carboxyl groups, and 0.1-30 parts by weight of an acrylic copolymer (copolymer B) comprising a (meth)acrylic acid alkyl ester as the main constituent component and a primary amino group and/or carboxyhydrazide group on a side chain, and containing no free carboxyl groups. The primary amino group and/or carboxyhydrazide on the side chain of copolymer B participates in crosslinking reaction with the carbonyl group of the diacetoneacrylamide in copolymer A, and it therefore functions as a crosslinking agent as well as a constituent component of the pressure-sensitive adhesive. Thus, it is an important feature of the crosslinkable pressure-sensitive adhesive for skin that crosslinking is possible without using a low molecular crosslinking agent.

A first example of copolymer B is an acrylic copolymer obtained by copolymerizing a (meth)acrylic acid alkyl ester as the main constituent component with a (meth)acrylic monomer having a primary amino group on a side chain.

A second example of copolymer B is an acrylic copolymer obtained by copolymerizing a (meth)acrylic acid alkyl ester as the main constituent component with (meth)acrylic acid, and then reacting the free carboxyl group in the obtained copolymer with an imine, diamine and/or dicarboxylic acid dihydrazide.

A third example of copolymer B is an acrylic copolymer obtained by copolymerizing a (meth)acrylic acid alkyl ester as the main constituent component with diacetoneacrylamide, and then reacting the carbonyl group in the obtained copolymer with a diamine and/or dicarboxylic acid dihydrazide.

The crosslinkable pressure-sensitive adhesive for skin of the invention which is formed on a sheet-like support is used as a medical patch. The crosslinkable pressure-sensitive adhesive sheet for skin may be manufactured by dissolving 100 parts by weight of copolymer A and 0.1-30 parts by weight of copolymer B in a solvent, and then evaporating off the solvent by heat according to a publicly known method. In this process, 25-200 parts by weight of a plasticizer with respect to 100 parts by weight of copolymer A, or a percutaneous absorbing medical component and/or cosmetic ingredient, percutaneous absorption accelerator, aromatic or the like may also be added.

The crosslinkable pressure-sensitive adhesive for skin of the invention is produced by first dissolving copolymer A and copolymer B in a solvent and evaporating off the solvent by heat according to a publicly known method. Because copolymer A and copolymer B undergo mild crosslinking reaction in the solvent, the solution cannot be stored for long periods. However, by adding a volatile ketone such as acetone or butanone to the solution at 5.0 wt % with respect to the total solvent, it is possible to prevent crosslinking reaction during storage and thus allow storage for prolonged periods. The present invention therefore provides a composition for production of a crosslinkable pressure-sensitive adhesive for skin capable of long-term storage, comprising copolymer A and copolymer B dissolved in a solvent comprising a volatile ketone such as acetone or butanone.

According to the invention, there is provided a crosslinkable pressure-sensitive adhesive for skin that has satisfactory adhesion and release properties for skin and low irritation to skin without using low molecular crosslinking agents, and a pressure-sensitive adhesive sheet for skin suitable for medical or cosmetic use. There is further provided a composition for production of a crosslinkable pressure-sensitive adhesive for skin that is stable even with prolonged storage.

The crosslinkable pressure-sensitive adhesive for skin of the invention has the following features. (1) Since copolymer A does not contain acrylic acid, does not have the excessively strong cohesion of acrylic acid-based pressure-sensitive adhesives and produces no carboxylic acid-induced skin irritation, it is therefore suitable for adhesion to skin. (2) When using a drug, the basic drug usually interacts with the acrylic acid in the acrylic acid-containing pressure-sensitive adhesive resulting in impaired stability or lowered percutaneous absorption property, but since the pressure-sensitive adhesive of the invention contains no acrylic acid such inconveniences do not arise. (3) Because a large amount of isocyanate-based crosslinking agent is not used as the crosslinking agent, there is no loss of stability due to reaction with the drug.

DETAILED DESCRIPTION OF THE PREFERRED EMBODIMENTS

Figure 1:
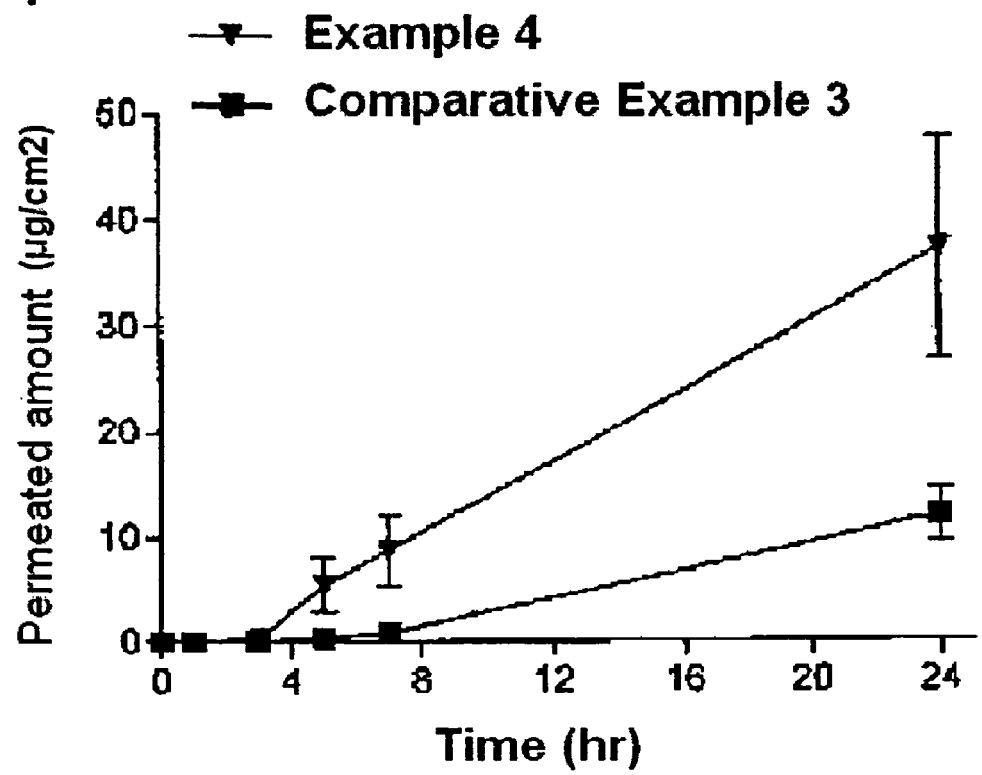
FIG. 1 is a graph showing the results of evaluating percutaneous absorption of oxybutynin using rat skin.

As examples of the (meth)acrylic acid alkyl ester of the acrylic copolymer (copolymer A) comprising a (meth)acrylic acid alkyl ester as the main constituent component and 3-45 wt % diacetoneacrylamide as an essential constituent component, and containing no free carboxyl groups, there may be mentioned butyl (meth)acrylate, isobutyl (meth)acrylate, hexyl acrylate, octyl acrylate, 2-ethylhexyl (meth)acrylate, isooctyl (meth)acrylate and decyl (meth)acrylate, any of which may be used alone or in combinations.

The content of the diacetoneacrylamide as the essential constituent component of copolymer A is 3-45 wt %, preferably 8-40 wt %, and more preferably 10-30 wt %. Below this lower limit, the crosslinking may not occur to a sufficient degree resulting in poor cohesion, and above this upper limit the cohesion will be too strong and lower the adhesion.

Copolymer A may also be copolymerized with 1.0-20 wt % of a polar monomer (for example, 2-vinylpyrrolidone, vinyl acetate, acrylamide or the like) in order to increase the solubility of the medical component or cosmetic ingredient in the pressure-sensitive adhesive.

Copolymer A can usually be prepared by solution polymerization of the required constituent components in the presence of a polymerization initiator. However, there is no limitation to this form of polymerization. The polymerization reaction conditions may be appropriately selected primarily depending on the types of constituent components. For solution polymerization, for example, ethyl acetate or another common polymerization solvent is added to a prescribed amount of the required constituent components, and reaction is conducted in a nitrogen atmosphere at 70-90° C. for 8-40 hours in a reactor equipped with a stirrer and a cooling reflux apparatus, in the presence of a polymerization initiator such as an azobis compound or peroxide. The constituent components and the solvent may be introduced at once or in appropriate portions. The polymerization initiator is preferably introduced in appropriate portions depending on progression of the reaction.

As examples of azobis-based polymerization initiators there may be mentioned 2,2'-azobis-isobutyronitrile, 1,1'-azobis(cyclohexane-1-carbonitrile) and 2,2'-azobis-(2,4-dimethylvaleronitrile), and as examples of peroxide-based polymerization initiators there may be mentioned lauroyl peroxide, benzoyl peroxide and di(tert-butyl) peroxide.

The acrylic copolymer (copolymer B) comprising a (meth)acrylic acid alkyl ester as the main constituent component and a primary amino group and/or carboxyhydrazide group on a side chain, and containing no free carboxyl groups, crosslinks with copolymer A by reaction with the diacetoneacrylamide ketone groups of copolymer A, while also serving as a constituent component of the crosslinkable pressure-sensitive adhesive for skin. The copolymer B may be prepared by a known process. The following processes may be mentioned as examples.

The first example of a preparation process involves using a (meth)acrylic acid alkyl ester such as butyl (meth)acrylate, 2-ethylhexyl (meth)acrylate or the like as the main constituent component and copolymerizing it with a monomer having a primary amino group on a side chain such as aminoethyl (meth)acrylate by an ordinary method. The copolymer obtained in this manner has a free primary amino group on a side chain.

The second example of a preparation process involves using a (meth)acrylic acid alkyl ester such as butyl (meth)acrylate, 2-ethylhexyl (meth)acrylate or the like as the main constituent component and copolymerizing it with (meth) acrylic acid by an ordinary method, and then modifying the carboxyl groups of the obtained copolymer using an imine, diamine and/or dicarboxylic acid dihydrazide. The apparatus, solvent, initiator and reaction conditions used for polymerization of the copolymer may be the same as for copolymer A. As examples of imines for modification of the obtained copolymer there may be mentioned alkyleneimines such as ethyleneimine and propyleneimine, with ethyleneimine being particularly preferred. As diamines there may be mentioned straight-chain alkylenediamines such as ethylenediamine, propylenediamine, butylenediamine, pentanediamine and hexanediamine, and cycloalkylenediamines such as cyclohexyldiamine, with hexanediamine being particularly preferred. As dicarboxylic acid dihydrazides there may be mentioned glutaric acid dihydrazide, adipic acid dihydrazide and pimelic acid dihydrazide, with adipic acid dihydrazide being particularly preferred. These imines, diamines and dicarboxylic acid dihydrazides may be used alone, or two or more components may be used in admixture. In the case of modification with an alkyleneimine, ester bonds are formed with the carboxyl groups in the copolymer, producing free primary amino groups on the side chains. In the case of modification with a diamine and/or dicarboxylic acid dihydrazide, the carboxyl groups in the copolymer form acid amide bonds with one of the amino of the diamine and/or dicarboxylic acid hydrazide and/or carboxylic acid dihydrazide groups, producing primary amino groups and/or carboxyhydrazide groups on side chains.

The third example of a preparation process is a process of copolymerizing a (meth)acrylic acid alkyl ester with diacetoneacrylamide, and then reacting the carbonyl groups in the obtained copolymer with a diamine and/or dicarboxylic acid dihydrazide. The diamine and dicarboxylic acid dihydrazide used in the process may be the same as described for the second preparation process example. These may be used alone, or two or more components may be used in admixture. The carbonyl group of the diacetoneacrylamide in the copolymer covalently bonds with one of the amino groups and/or carboxylic acid hydrazide group of the diamine and/or dicarboxylic acid dihydrazide, producing free primary amino groups and/or carboxylic acid hydrazide groups on side chains.

These processes for production of copolymer B are merely for illustration and are not intended to be restrictive. Any method may be employed to produce the acrylic copolymer comprising a (meth)acrylic acid alkyl ester as the main constituent component and a primary amino group and/or carboxyhydrazide group on a side chain, and containing no free carboxyl groups. The copolymer B obtained in this manner may be purified if necessary to remove the unreacted imine, diamine and dicarboxylic acid dihydrazide prior to use.

Since it is important for the copolymer B to dissolve in the same solvent as the copolymer A and have high compatibility therewith, it must comprise a (meth)acrylic acid alkyl ester as the main constituent component. The molecular weight is preferably 2000 or greater in order to exhibit properties as a polymer crosslinking agent. If the molecular weight is less than 2000, the difference in performance compared to low molecular polyamines will be minimal and the effect of the invention will not be exhibited. The primary amino group and/or carboxyhydrazide group in copolymer B must be present at a density of at least 2, and preferably 3, per molecule of copolymer B in order to exhibit a suitable crosslinking property with copolymer A. The primary amino group and/or carboxyhydrazide group in copolymer B are also preferably included at a density of one per 5-100 molecules of the (meth)acrylic acid alkyl ester comonomers that comprise the main component of copolymer B. If the proportion of addition of copolymer B with respect to copolymer A is too low, the reinforcing effect of the addition on cohesion will be not be readily exhibited, and if it is too large the adhesion will be reduced, and therefore copolymer B is added at 0.1-30 parts by weight and preferably 0.3-20 parts by weight with respect to 100 parts by weight of copolymer A. The crosslinking of copolymer A by copolymer B according to the invention occurs as carbonyl groups of the diacetone acrylamide in copolymer A form covalent bonds by dehydration reaction with the free primary amino groups and/or carboxylic acid hydrazide groups on the side chains of copolymer B.

The pressure-sensitive adhesive sheet for skin according to the invention is constructed by laminating a pressure-sensitive adhesive layer made of a crosslinkable pressure-sensitive adhesive for skin on at least one side of a sheet-like support, and it may be suitably used as a pressure-sensitive adhesive sheet for skin, for adhesive plaster, dressings and the like. Medical and/or cosmetic ingredients may also be added to produce percutaneous absorption preparations, cosmetic patches and the like.

The support for the pressure-sensitive adhesive sheet for skin is preferably soft and impermeable or only semipermeable to drugs, and for example, there may be mentioned resin films such as polyethylene, ethylene-vinyl acetate copolymer, ethylene-vinyl acetate-carbon monoxide copolymer, ethylene-butyl acrylate-carbon monoxide copolymer, nylon, polyethylene terephthalate and polybutylene terephthalate, as well as aluminum sheets, which may be used as laminated sheets or as laminates with woven fabrics or nonwoven fabrics. In order to increase adhesion with the pressure-sensitive adhesive layer, the support may be subjected to surface treatment such as corona treatment or plasma discharge treatment, or to anchor coat treatment with an anchoring agent.

The crosslinkable pressure-sensitive adhesive for skin of the invention may also include a plasticizer. Addition of a plasticizer can further reduce irritation of the skin by the crosslinkable pressure-sensitive adhesive for skin, and can improve percutaneous absorption of a drug impregnated therein. The plasticizer is preferably added at 25-200 parts by weight to 100 parts by weight of copolymer A. If the amount is less than 25 parts by weight the intended effect will not be easily achieved, and if it is greater than 200 parts by weight, the pressure-sensitive adhesive will tend to lack cohesion even with crosslinking as described hereunder.

As examples of plasticizers there may be mentioned fatty acid esters of monohydric alcohols such as cetyl octanoate, hexyl laurate, isopropyl myristate, isopropyl palmitate, butyl stearate and myristyl lactate; dibasic acid esters such as dioctyl adipate, diethyl sebacate, dioctyl sebacate and dioctyl succinate; and fatty acid esters of polyhydric alcohols such as propyleneglycol dicaproate, glyceryl trioctanoate, glyceryl tri(octanoate/decanoate), medium chain fatty acid triglycerides and the like, among which fatty acid esters such as isopropyl myristate, isopropyl palmitate, diethyl sebacate and medium chain fatty acid triglycerides are particularly preferred.

The medical components to be included in the crosslinkable pressure-sensitive adhesive for skin are not particularly restricted so long as they can permeate biological membranes in the skin, and as examples there may be mentioned general anesthetics, hypnotics/analgesics, anti-epileptic agents, antipyretic analgesic anti-inflammatory agents, steroidal anti-inflammatory drugs, stimulants/analeptics, anti-motion sickness agents, psychoneurotic drugs, local anesthetics, skeletal muscle relaxants, autonomic nerve agents, antispasmodic drugs, anti-Parkinson drugs, antihistamines, cardiac stimulants, anti-arrhythmia drugs, diuretics, antihypertensive agents, vasoconstrictors, vasodilators, anti-arteriosclerotic agents, respiratory stimulants, antitussive expectorants, peptic ulcer treatment agents, cholagogues, hormone agents, urogenital and anal drugs, anti-asthmatic drugs, parasitic skin disease drugs, emollients, vitamins, inorganic preparations, hemostatic drugs, anti-coagulants, liver disease drugs, drug addiction agents, anti-gout agents, anti-diabetes agents, anti-malignant tumor agents, radioactive medicines, Chinese herbal preparations, antibiotics, chemotherapeutic agents, vermifuges/antiprotozoal agents, narcotics, and the like.

As examples of antipyretic analgesic anti-inflammatory agents there may be mentioned ibuprofen, naproxen, flurbiprofen, ketoprofen and amfenac sodium, and as examples of steroidal anti-inflammatory drugs there may be mentioned hydrocortisone, triamcinolone, dexamethasone, betamethasone and prednisolone.

As examples of vasodilators there may be mentioned diltiazem hydrochloride, pentaerythritol tetranitrate and isosorbide nitrate. As examples of anti-arrhythmia drugs there may be mentioned procainamide hydrochloride, diisopyramide and mexiletine hydrochloride. As examples of antihypertensive agents there may be mentioned clonidine hydrochloride, bunitrolol hydrochloride and captopril.

As examples of local anesthetics there may be mentioned ethyl aminobenzoate, tetracaine hydrochloride, procaine hydrochloride, dibucaine hydrochloride, oxybuprocaine hydrochloride and propitocaine hydrochloride. As examples of hormone agents there may be mentioned estradiol, estriol and progesterone. As an example of a urinary drug there may be mentioned oxybutynin, as an example of an anti-asthmatic drug there may be mentioned tulobuterol, and as examples of antihistamines there may be mentioned diphenhydramine hydrochloride, chlorpheniramine maleate, promethazine, cyproheptadine hydrochloride and diphenylpyraline hydrochloride. As examples of anti-coagulants there may be mentioned warfarin potassium and ticlopidine hydrochloride.

As examples of general anesthetics there may be mentioned thiopental sodium and pentobarbital sodium. As examples of hypnotics/analgesics there may be mentioned bromovalerylurea, amobarbital and phenobarbital. As an example of an anti-epileptic agent there may be mentioned phenyloin sodium. As an example of a stimulant/analeptic there may be mentioned methamphetamine hydrochloride. As examples of anti-motion sickness agents there may be mentioned diphenidol hydrochloride and betahistamine mesylate.

As examples of psychoneurotic drugs there may be mentioned chlorpromazine hydrochloride, thioridazine, meprobamate, imipramine hydrochloride, chlordiazepoxide and diazepam. As examples of skeletal muscle relaxants there may be mentioned suxamethonium hydrochloride and eperisone hydrochloride. As examples of autonomic nerve agents there may be mentioned neostigmine bromide and bethanechol hydrochloride. As an example of an anti-Parkinson drug there may be mentioned amantadine hydrochloride. As examples of diuretics there may be mentioned hydroflumethiazide, isosorbide and furosemide.

As an example of a vasoconstrictor there may be mentioned phenylephrine hydrochloride. As examples of respiratory stimulants there may be mentioned lobeline hydrochloride, dimorpholamine and naloxone hydrochloride. As examples of narcotics there may be mentioned morphine hydrochloride, codeine phosphate, cocaine hydrochloride and pethidine hydrochloride.

As examples of cosmetic ingredients to be contained in crosslinkable pressure-sensitive adhesives for skin there may be mentioned whitening ingredients such as ascorbyl palmitate, kojic acid, lucinol, tranexamic acid and oil-soluble licorice extract, wrinkle preventers such as retinol, retinoic acid, retinol acetate and retinol palmitate, circulation improving ingredients such as vitamin E, tocopherol acetate, capsaicin and vanillylamide nonylate, antimicrobial ingredients such as isopropylmethylphenol, light-sensitive elements and zinc oxide, and vitamins such as vitamin $D_2$, vitamin $D_3$ and vitamin K.

The content of a medical or cosmetic ingredient in the crosslinkable pressure-sensitive adhesive for skin may be appropriately determined according to the type and purpose of use, but in too small an amount the effectiveness will be reduced while in too large an amount the adhesive property will be reduced, and therefore they are preferably added at 0.01-50 wt % in the pressure-sensitive adhesive layer. No particular problem results if the medical or cosmetic ingredient is in a supersaturated state or in a precipitated crystal state in the pressure-sensitive adhesive layer. Medical and cosmetic ingredients may also be encapsulated together with absorption accelerators, or a retaining layer may be provided for the medical or cosmetic ingredients.

A percutaneous absorption preparation or cosmetic patch obtained using a pressure-sensitive adhesive for skin according to the invention may also contain added percutaneous absorption accelerators, drug dissolution aids or preventers, aromatic agents, and the like. The thickness of the pressure-sensitive adhesive layer for skin of the invention is not particularly restricted. However, if it is too thin the drug or cosmetic ingredient content must be increased and the adhesion will be reduced. If it is too thick, the medical or cosmetic ingredient in the pressure-sensitive adhesive near the support will not readily diffuse to the pressure-sensitive adhesive layer surface, thereby lowering the drug release property. In most cases, the thickness is preferably 10-200 μm.

A percutaneous absorption preparation or cosmetic patch of the invention may be produced by a pressure-sensitive adhesive tape production process known in the prior art. In a solution coating method, for example, prescribed amounts of a plasticizer, medical or cosmetic ingredient, and the like are mixed with a solution containing the copolymer A and copolymer B, if necessary with dilution using an organic solvent, and the obtained solution is used for coating and drying onto a support, or is coated and dried on a release sheet and then transferred to a support.

The composition for production of a crosslinkable pressure-sensitive adhesive for skin according to the invention is obtained by dissolving copolymer A and copolymer B in a solvent. The solvent may be any solvent used for polymerization of copolymers, and for example, ethyl acetate or the like may be used without modification. The solvent may be a simple solvent or a mixed solvent.

When copolymer A and copolymer B are mixed and dissolved in an ordinary solvent (for example, ethyl acetate or toluene), copolymer A is gradually crosslinked by copolymer B in the solution, resulting in gelling of the solution, and therefore preparation before use is necessary before coating. This is similar to the case where ordinary low molecular crosslinking agent is used. According to the invention, there is provided a composition for production of a crosslinkable pressure-sensitive adhesive for skin obtained by further adding a ketone such as acetone or butanone to a solution comprising 100 parts by weight of copolymer A, 0.1-30 parts by weight of copolymer B and a prescribed amount of solvent (for example, the polymerization solvent ethyl acetate). This is based on the novel finding that acetone, butanone and the like prevent crosslinking reaction of copolymer A by copolymer B, thereby allowing the composition for production of a crosslinkable pressure-sensitive adhesive for skin to be stored for prolonged periods. The ketone used in this case is preferably one that readily evaporates off when evaporating the solution of copolymer A and copolymer B by heat to produce the pressure-sensitive adhesive for skin, and acetone, butanone and mixtures thereof are suitable for this purpose. By dissolving copolymer A and copolymer B, with a plasticizer and medical or cosmetic ingredients as necessary, in a solvent such as ethyl acetate or toluene and adding acetone and/or butanone prior to storage of the solution, preparation of the solution before use is no longer necessary and working efficiency is significantly improved.

When acetone and/or butanone is added to the solvent dissolving copolymer A and copolymer B, the acetone and/or butanone inhibits crosslinking reaction between the ketone groups in the diacetoneacrylamide of copolymer A and the primary amino groups or carboxyhydrazide groups on the side chains of copolymer B. As a result, the composition can be stored for prolonged periods without gelling. The content of acetone and/or butanone is preferably at least 5 wt % with respect to the total weight of the mixed solvent. If the content is too low, the storage property of the composition for production of a crosslinkable pressure-sensitive adhesive for skin will be reduced.

EXAMPLES

Examples of the present invention will now be explained in detail. Throughout the examples, the parts and percentage values are based on weight.

Copolymer A Production Example 1

A mixture comprising 200 parts of 2-ethylhexyl acrylate, 100 parts of butyl acrylate and 50 parts of diacetoneacrylamide as monomers and 300 parts of ethyl acetate as the solvent was supplied to a separable flask equipped with a stirrer and reflux condenser, and the temperature was raised to 75° C. with stirring and nitrogen replacement. A solution of 2 parts of benzoyl peroxide in 20 parts of ethyl acetate was divided into 5 portions, and one was added to the separable flask to initiate polymerization. The remaining four portions were added one at a time at each hour beginning at the second hour after start of the reaction, and upon completion of the addition, reaction was continued for 2 hours. For adjustment of the viscosity, 50 parts of ethyl acetate was added four times, every two hours after start of the reaction. Upon completion of the reaction, the mixture was cooled and ethyl acetate was added to obtain a solution of copolymer A having a solid concentration of 30 wt %, and a styrene-based weight-average molecular weight of $110\times10^4$ cps as measured by gel permeation chromatography (GPC).

Copolymer A Production Example 2

A monomer composition comprising 150 parts of 2-ethylhexyl acrylate, 100 parts of butyl acrylate, 50 parts of diacetoneacrylamide and 50 parts of vinyl acetate was used in the same manner as Copolymer A Production Example 1 to obtain a solution of copolymer A having a solid concentration of 30 wt % and a styrene-based weight-average molecular weight of $95\times10^4$ cps as measured by GPC.

Copolymer A Production Example 3

A monomer composition comprising 150 parts of 2-ethylhexyl acrylate, 150 parts of butyl acrylate and 100 parts of diacetoneacrylamide was used, with lauroyl peroxide as a polymerization initiator, in the same manner as Copolymer A Production Example 1 to obtain a solution of copolymer A having a solid concentration of 30 wt % and a styrene-based weight-average molecular weight of $95\times10^4$ cps as measured by GPC.

Copolymer B Production Example 1

A mixture comprising 200 parts of 2-ethylhexyl acrylate, 100 parts of butyl acrylate and 30 parts of aminoethyl methacrylate as monomers and 300 parts of isopropyl acetate as the solvent was supplied to a separable flask equipped with a stirrer and reflux condenser, and the temperature was raised to 80° C. with stirring and nitrogen replacement. A solution of 2 parts of benzoyl peroxide in 30 parts of ethyl acetate was divided into 5 portions, and one was added to the separable flask to initiate polymerization. The remaining four portions were added one at a time at each hour beginning at the second hour after start of the reaction, and upon completion of the addition, reaction was continued for 2 hours. For adjustment of the viscosity, 50 parts of isopropyl acetate was added four times, every two hours after start of the reaction. Upon completion of the reaction, the mixture was cooled and ethyl acetate was added to obtain a solution of copolymer B having a solid concentration of 30 wt %, and a styrene-based weight-average molecular weight of $12\times10^4$ cps as measured by GPC.

Copolymer B Production Example 2

A monomer composition comprising 200 parts of 2-ethylhexyl acrylate, 100 parts of butyl acrylate and 10 parts of acrylic acid, with addition of 20 parts of dodecylmercaptan as a molecular weight adjustor, was used in the same manner as Copolymer B Production Example 1 to obtain a solution of copolymer B having a solid concentration of 30 wt % and a styrene-based weight-average molecular weight of $9\times10^3$ cps as measured by GPC. After adding 10 parts of ethyleneimine and 5 parts of concentrated hydrochloric acid to the solution, reaction was conducted at 80° C. for 5 hours. Upon completion of the reaction, the mixture was cooled and washed three times with purified water, and then ethyl acetate was added to obtain a solution of copolymer B with a solid concentration of 30 wt %.

Copolymer B Production Example 3

A mixture comprising 660 parts of ethyl acrylate and 70 parts of diacetoneacrylamide as the monomer composition, with addition of 40 parts of dodecylmercaptan as a molecular weight adjustor and 400 parts of ethyl acetate as a solvent, was supplied to a separable flask equipped with a stirrer and reflux condenser, and the temperature was raised to 70° C. with stirring and nitrogen replacement. A solution of 5 parts of azobisisobutyronitrile in 100 parts of ethyl acetate was divided into 5 portions, and one was added to the separable flask to initiate polymerization. The remaining four portions were added one at a time at each hour beginning at the second hour after start of the reaction, and upon completion of the addition, reaction was continued for 2 hours. For adjustment of the viscosity, 50 parts of ethyl acetate was added four times, every two hours after start of the reaction. Upon completion of the reaction, the mixture was cooled and a solution of 40 parts of adipic acid dihydrazide dissolved in a mixture of 40 parts of purified water, 1600 parts of methanol and 260 parts of ethyl acetate was added to a separable flask, 5 parts of concentrated hydrochloric acid was further added, and the temperature was raised to 70° C.

Upon completion of the reaction, the mixture was cooled and washed three times with purified water, and then the product was dissolved in a mixed solvent of 700 parts of ethyl acetate, 1400 parts of acetone and 400 parts of methanol, to obtain a solution of copolymer B having a solid concentration of 30 wt %, and a styrene-based weight-average molecular weight of $12 \times 10^4$ cps as measured by GPC.

Comparative Production Example 1

A monomer composition comprising 150 parts of 2-ethylhexyl acrylate, 100 parts of butyl acrylate and 15 parts of acrylic acid was used in the same manner as Copolymer A Production Example 1 to obtain a solution of a copolymer having a solid concentration of 30 wt % and a styrene-based weight-average molecular weight of $125 \times 10^4$ cps as measured by GPC.

Comparative Production Example 2

A monomer composition comprising 100 parts of 2-ethylhexyl acrylate, 100 parts of butyl acrylate, 50 parts of vinyl acetate and 10 parts of acrylic acid was used in the same manner as Copolymer A Production Example 1 to obtain a solution of a copolymer having a solid concentration of 30 wt % and a styrene-based weight-average molecular weight of $95 \times 10^4$ cps as measured by GPC.

Comparative Production Example 3

Except for using 5 parts of diacetoneacrylamide, the procedure was carried out in the same manner as Copolymer A Production Example 1 to obtain a solution of a copolymer having a solid concentration of 30 wt % and a styrene-based weight-average molecular weight of $85 \times 10^4$ cps as measured by GPC.

Example 1

After adding 5 parts of the solution obtained in Copolymer B Production Example 1 to 100 parts of the solution obtained in Copolymer A Production Example 1, the two solutions were uniformly stirred with a dissolver to obtain a mixture. The obtained mixture was coated onto a silicone-treated PET (polyethylene terephthalate) film with a thickness of 35 μm to a post-drying pressure-sensitive adhesive layer thickness of 100 μm and dried, and then the pressure-sensitive adhesive layer was laminated on the PET layer of a PET/EVA (ethylenevinyl acetate copolymer) laminated film with a thickness of 35 μm to obtain a pressure-sensitive adhesive sheet for skin.

Example 2

After adding 4 parts of the solution obtained in Copolymer B Production Example 1 and 20 parts of isopropyl myristate as a plasticizer to 100 parts of the solution obtained in Copolymer A Production Example 1, the components were uniformly stirred with a dissolver to obtain a mixture. The obtained mixture was used for the same procedure as in Example 1 to obtain a pressure-sensitive adhesive sheet for skin.

Example 3

After adding 4 parts of the solution obtained in Copolymer B Production Example 2 and 30 parts of isopropyl palmitate as a plasticizer to 100 parts of the solution obtained in Copolymer A Production Example 2, the components were uniformly stirred with a dissolver to obtain a mixture. The obtained mixture was used for the same procedure as in Example 1 to obtain a pressure-sensitive adhesive sheet for skin.

Example 4

After adding 2 parts of the solution obtained in Copolymer B Production Example 1 and 15 parts of oxybutynin as a drug to 100 parts of the solution obtained in Copolymer A Production Example 1, the components were uniformly stirred with a dissolver to obtain a mixture. The obtained mixture was used for the same procedure as in Example 1 to obtain a drug-containing pressure-sensitive adhesive sheet for skin.

Example 5

After adding 3 parts of the solution obtained in Copolymer B Production Example 2 and 10 parts of tulobuterol as a drug to 100 parts of the solution obtained in Copolymer A Production Example 2, the components were uniformly stirred with a dissolver to obtain a mixture. The obtained mixture was used for the same procedure as in Example 1 to obtain a drug-containing pressure-sensitive adhesive sheet for skin.

Example 6

After adding 3 parts of the solution obtained in Copolymer B Production Example 1 and 10 parts of acetone (approximately 12 wt % of the total solvent) to 100 parts of the solution obtained in Copolymer A Production Example 1, the components were uniformly stirred with a dissolver to obtain a mixture. The mixture was placed in a sealed glass bottle and kept at room temperature for 3 months. The mixture exhibited no tendency toward viscosity increase or any signs of solution gelling even after 3 months.

Example 7

After adding 3 parts of the solution obtained in Copolymer B Production Example 2 and 30 parts of butanone (approximately 30 wt % of the total solvent) to 100 parts of the solution obtained in Copolymer A Production Example 2, the components were uniformly stirred with a dissolver to obtain a mixture. The mixture was placed in a sealed glass bottle and kept at room temperature for 3 months. The mixture exhibited no tendency toward viscosity increase or any signs of solution gelling even after 3 months.

Example 8

After adding 4 parts of the solution obtained in Copolymer B Production Example 2, 20 parts of glyceryl trioctanoate as a plasticizer and 10 parts of ketoprofen as a drug to 100 parts of the solution obtained in Copolymer A Production Example 2, the components were uniformly stirred with a dissolver to obtain a mixture. The obtained mixture was used for the same procedure as in Example 1 to obtain a drug-containing pressure-sensitive adhesive sheet for skin.

Example 9

After adding 10 parts of the solution obtained in Copolymer B Production Example 3 to 100 parts of the solution obtained in Copolymer A Production Example 3, the two solutions were uniformly stirred with a dissolver to obtain a mixture. The obtained mixture was used for the same procedure as in Example 1 to obtain a pressure-sensitive adhesive sheet for skin.

Example 10

After adding 3 parts of the solution obtained in Copolymer B Production Example 3 and 15 parts of isopropyl myristate as a plasticizer to 100 parts of the solution obtained in Copolymer A Production Example 3, the components were uniformly stirred with a dissolver to obtain a mixture. The obtained mixture was used for the same procedure as in Example 1 to obtain a pressure-sensitive adhesive sheet for skin.

Example 11

After adding 10 parts of the solution obtained in Copolymer B Production Example 3, 20 parts of isopropyl myristate as a plasticizer and 10 parts of ketoprofen as a drug to 100 parts of the solution obtained in Copolymer A Production Example 3, the components were uniformly stirred with a dissolver to obtain a mixture. The obtained mixture was used for the same procedure as in Example 1 to obtain a drug-containing pressure-sensitive adhesive sheet for skin.

Example 12

After adding 5 parts of the solution obtained in Copolymer B Production Example 3 and 2 parts of acetone (approximately 5 wt % of the total solvent) to 100 parts of the solution obtained in Copolymer A Production Example 3, the components were uniformly stirred with a dissolver to obtain a mixture. The mixture was placed in a sealed glass bottle and kept at room temperature for 3 months. The mixture exhibited no tendency toward viscosity increase or any signs of solution gelling even after 3 months.

Example 13

After adding 10 parts of the solution obtained in Copolymer B Production Example 3 and 6 parts of acetone (approximately 10 wt % of the total solvent) to 100 parts of the solution obtained in Copolymer A Production Example 3, the components were uniformly stirred with a dissolver to obtain a mixture. The mixture was placed in a sealed glass bottle and kept at room temperature for 3 months. The mixture exhibited no tendency toward viscosity increase or any signs of solution gelling even after 3 months.

Comparative Example 1

After adding 0.5 part of a trifunctional polyisocyanate (Coronate HL, Nippon Polyurethane Industry Co., Ltd.) as a crosslinking agent to 100 parts of the copolymer solution obtained in Comparative Production Example 1, the components were uniformly stirred with a dissolver to obtain a mixture. The obtained mixture was used for the same procedure as in Example 1 to obtain a pressure-sensitive adhesive sheet for skin.

Comparative Example 2

After dissolving 0.5 part of aluminum acetylacetonate as a crosslinking agent in acetylacetone and adding the solution to 100 parts of the copolymer solution obtained in Comparative Production Example 2, the two solutions were uniformly stirred with a dissolver to obtain a mixture. The obtained mixture was used for the same procedure as in Example 1 to obtain a pressure-sensitive adhesive sheet for skin.

Comparative Example 3

After adding 15 parts of oxybutynin as a drug to 100 parts of the mixture obtained in Comparative Example 1, the components were uniformly stirred with a dissolver to obtain a mixture. The obtained mixture was used for the same procedure as in Example 1 to obtain a drug-containing pressure-sensitive adhesive sheet for skin.

Comparative Example 4

After adding 10 parts of tulobuterol as a drug to 100 parts of the mixture obtained in Comparative Example 2, the components were uniformly stirred with a dissolver to obtain a mixture. The obtained mixture was used for the same procedure as in Example 1 to obtain a drug-containing pressure-sensitive adhesive sheet for skin.

Comparative Example 5

The mixture obtained in Comparative Example 1 was placed in a sealed glass bottle and kept at room temperature, and after 2 days the solution gelled and lost fluidity, making it impossible for coating to obtain a sheet.

Comparative Example 6

After adding 3 parts of the solution obtained in Copolymer B Production Example 1 and 30 parts of isopropyl palmitate as a plasticizer to 100 parts of the copolymer solution obtained in Comparative Production Example 3, the components were uniformly stirred with a dissolver to obtain a mixture. The obtained mixture was used for the same procedure as in Example 1 to obtain a pressure-sensitive adhesive sheet for skin.

Comparative Example 7

After adding 0.05 part of the solution obtained in Copolymer B Production Example 1 and 30 parts of isopropyl palmitate as a plasticizer to 100 parts of the solution obtained in Copolymer A Production Example 2, the components were uniformly stirred with a dissolver to obtain a mixture. The obtained mixture was used for the same procedure as in Example 1 to obtain a pressure-sensitive adhesive sheet for skin.

Comparative Example 8

After adding 3 parts of a 1% aqueous solution of adipic acid dihydrazide as a crosslinking agent to 100 parts of the solution obtained in Copolymer A Production Example 1, 30 parts of isopropyl palmitate was added to the obtained mixture as a plasticizer and the components were uniformly stirred with a dissolver to obtain a mixture. The procedure thereafter was carried out in the same manner as Example 1 in an attempt to obtain a pressure-sensitive adhesive sheet for skin, but the solution separated and could not be satisfactorily coated, and therefore the procedure was terminated.

Comparative Example 9

A drug-containing pressure-sensitive adhesive sheet was obtained in the same manner as Example 8, except that 0.5 part of hexanediamine was added instead of copolymer B obtained in Copolymer B Production Example 2.

Comparative Example 10

After adding 3 parts of the solution obtained in Copolymer B Production Example 1 and 1 part of acetone (approximately 1.4 wt % of the total solvent) to 100 parts of the solution obtained in Copolymer A Production Example 1, the components were uniformly stirred with a dissolver to obtain a mixture. The mixture was placed in a sealed glass bottle and kept at room temperature. After one week, the mixture exhibited viscosity increase and gelled. This result demonstrated that prolonged storage cannot be achieved if the amount of added acetone is too small.

Comparative Example 11

After adding 3 parts of the solution obtained in Copolymer B Production Example 3 to 100 parts of the solution obtained in Copolymer A Production Example 3, the two solutions were uniformly stirred with a dissolver to obtain a mixture. The mixture was placed in a sealed glass bottle and kept at room temperature. After one day, the mixture exhibited viscosity increase and gelled. This result demonstrated that prolonged storage cannot be achieved if no acetone or the like is added.

The obtained medical patch for skin and percutaneous absorption preparation were subjected to a skin irritation test, adhesive residue test and peelability test in the manner described below, yielding the results shown in Table 1.

[Skin Irritation Test]

A test piece (10 cm² area) of the pressure-sensitive adhesive sheet (tape preparation) was attached to the shaven backs of each of four Japanese white rabbits, and after 24 hours it was peeled off and erythema of the skin was visually observed immediately and one hour after peeling. No edema or scab formation was observed in this test. The degree of erythema was evaluated according to the following 5-level scale (0-4).
0: No erythema, 1: Slightly discernible, very mild erythema, 2: Apparent erythema, 3: Moderate erythema, 4: Deep erythema The average determined by dividing the total score by the number of rabbits (four) was recorded as the skin irritation index for each tape preparation.

[Adhesive Residue Test]

The presence of adhesive residue on the skin immediately after peeling was visually observed during the skin irritation test described above. The evaluation scale used was the following.
0: No adhesive residue, 1: Very light adhesive residue, 2: Extensive adhesive residue The average determined by dividing the total score by the number of rabbits (four) was recorded as the adhesive residue index for each tape preparation.

[Peelability Test]

The condition of peeling of the test tape preparation from the skin immediately before peeling was visually observed during the skin irritation test described above. "No peeling" was defined as complete attachment of the test tape preparation to the rabbit skin. The evaluation scale used was the following.
0: No peeling, 1: Very slight peeling, 2: Extensive peeling The average determined by dividing the total score by the number of rabbits (four) was recorded as the peelability index for each tape preparation.

In Comparative Examples 6, 7 and 9, adhesive residue was found on the entire attached surface, and skin irritation was not measured. This was because virtually no crosslinking reaction had occurred in these samples.

TABLE 1

| | Pressure-sensitive adhesive | Evaluation results | | |
|---|---|---|---|---|
| | | Skin irritation index | Adhesive residue index | Peelability index |
| Examples | Example 1 | 1.5 | 0 | 0 |
| | Example 2 | 0.75 | 0 | 0 |
| | Example 3 | 0.5 | 0 | 0 |
| | Example 4 | 0.75 | 0 | 0 |
| | Example 5 | 1.0 | 0 | 0 |
| | Example 6 | 1.25 | 0 | 0 |
| | Example 7 | 1.5 | 0 | 0 |
| | Example 8 | 1.0 | 0 | 0 |
| | Example 9 | 1.0 | 0 | 0 |
| | Example 10 | 0 | 0 | 0 |
| | Example 11 | 0 | 0 | 0 |
| Comp. Examples | Comp. Ex. 1 | 2.0 | 0 | 1.0 |
| | Comp. Ex. 2 | 2.25 | 0 | 1.25 |
| | Comp. Ex. 3 | 2.5 | 0 | 1.0 |
| | Comp. Ex. 4 | 2.0 | 0 | 0.75 |
| | Comp. Ex. 6 | — | 2 | 0 |
| | Comp. Ex. 7 | — | 2 | 0 |
| | Comp. Ex. 9 | — | 2 | 0 |

[In Vitro Percutaneous Absorption Test]

The samples produced in Examples 4 and 5 and Comparative Examples 3 and 4 were used for a rat skin permeability test. A Franz diffusion cell with a diffusion cross-sectional area of 3.14 cm² was used for the test. The permeation membrane used was Wistar male rat shaved abdominal skin, and the receptor solution used was isotonic sodium chloride solution+polyethylene glycol 600 (volume ratio=80:20). A sample was attached to the corneum side of the rat skin, 100 μl of receptor solution was taken at fixed periods thereafter, and the concentration of drug which diffused through the rat skin and migrated into the receptor solution was measured by high performance liquid chromatography (HPLC).

(HPLC Measurement Conditions)
Column: ODS reversed phase partition column
Oxybutynin mobile phase: Phosphate buffer (pH 2.0)+acetonitrile (volume ratio=58:42)
Tulobuterol mobile phase: Phosphate buffer (pH 2.0)+acetonitrile (volume ratio=82:18)
Oxybutynin detection: Ultraviolet light at 240 nm
Tulobuterol detection: Ultraviolet light at 210 nm

[In Vitro Percutaneous Absorption Test Results]

Figure 2:
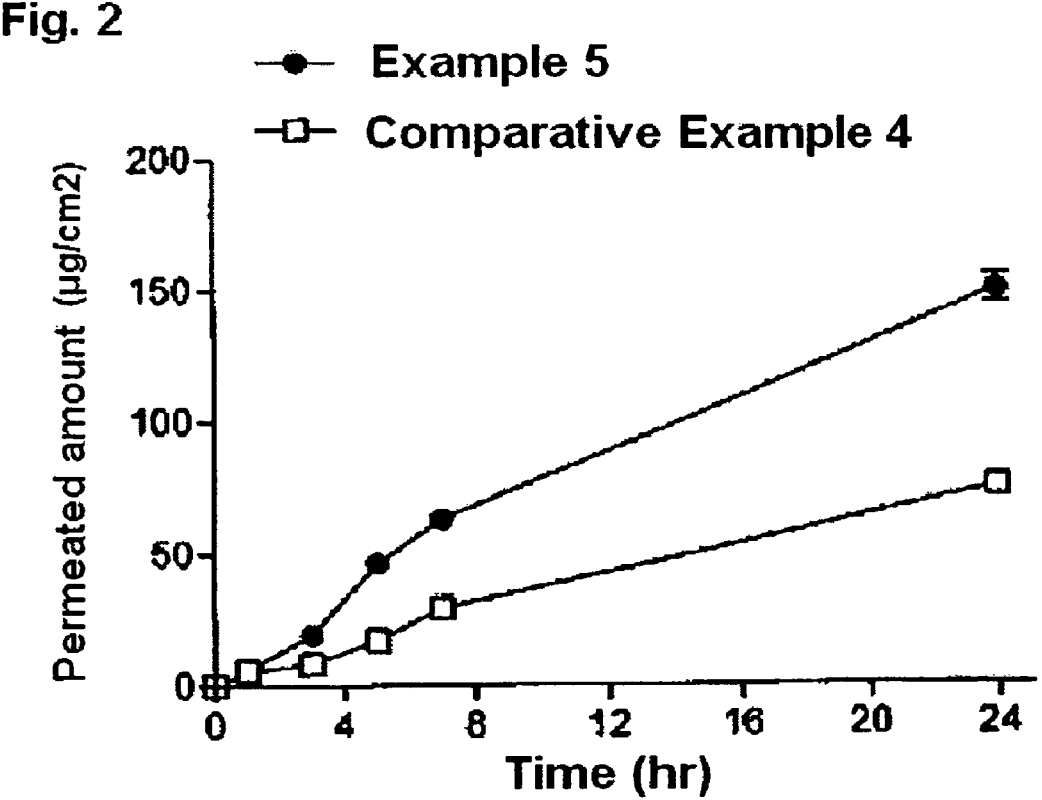
FIG. 2 is a graph showing the results of evaluating percutaneous absorption of tulobuterol using rat skin.

The obtained results are shown in FIG. 1 (oxybutynin) and FIG. 2 (tulobuterol). A clear increase in drug permeation level was seen in the examples against the comparative examples. It is believed that in the comparative examples, the acrylic acid and drug interacted and interfered with release of the drug from the pressure-sensitive adhesive.

INDUSTRIAL APPLICABILITY

There is provided a crosslinkable pressure-sensitive adhesive for skin that exhibits satisfactory adhesion and releasability for human skin and low irritation to skin, and a crosslinkable pressure-sensitive adhesive sheet for skin that is suitable for medical and cosmetic use. There is also provided a composition for production of a crosslinkable pressure-sensitive adhesive for skin that has superior storage properties and is suitable for preparation of the aforementioned crosslinkable pressure-sensitive adhesive for skin.

What is claimed is:

1. A precursor composition for a crosslinkable pressure-sensitive adhesive for skin, consisting of:
   i) an acrylic copolymer (copolymer A) comprising a (meth) acrylic acid alkyl ester as the main constituent component and 3-45 wt % diacetone acrylamide as an essential constituent component, and containing no free carboxyl groups; and
   ii) an acrylic copolymer (copolymer B) comprising a (meth)acrylic acid alkyl ester as the main constituent component and a primary amino group and/or carboxyhydrazide group on a side chain, and containing no free carboxyl groups, wherein the primary amino group and/or carboxyhydrazide group is present at a density of at least 2 per molecule of copolymer B and the primary amino group and/or carboxyhydrazide group in copolymer B is included at a density of one per 5-100 molecules of (meth)acrylic acid alkyl ester comonomer in copolymer B, wherein the molecular weight of copolymer B is at least 2000;
   wherein the proportion by weight of copolymer B with respect to copolymer A is 0.1-30:100, and wherein copolymers A and B are dissolved in a solvent.

2. The adhesive precursor composition according to claim 1, wherein the solvent contains acetone and/or butanone, and the amount of acetone and/or butanone is at least 5.0 wt % with respect to the total amount of the solvent.

3. The precursor composition according to claim 1, wherein the solvent contains acetone and/or butanone, and the amount of acetone and/or butanone is 5.0-30 wt % with respect to the total amount of the solvent.

4. A precursor composition for a crosslinkable pressure-sensitive adhesive for skin, comprising:
   i) an acrylic copolymer (copolymer A) comprising a (meth) acrylic acid alkyl ester as the main constituent component and 3-45 wt % diacetone acrylamide as an essential constituent component, and containing no free carboxyl groups; and
   ii) an acrylic copolymer (copolymer B) comprising a (meth)acrylic acid alkyl ester as the main constituent component and a carboxyhydrazide group on a side chain, and containing no free carboxyl groups, wherein the carboxyhydrazide group is present at a density of at least 2 per molecule of copolymer B and the carboxyhydrazide group in copolymer B is included at a density of one per 5-100 molecules of (meth)acrylic acid alkyl ester comonomer in copolymer B, wherein the molecular weight of copolymer B is at least 2000;
   wherein the proportion by weight of copolymer B with respect to copolymer A is 0.1-30:100, and wherein copolymers A and B are dissolved in a solvent.

5. The precursor composition according to claim 4, wherein the solvent contains acetone and/or butanone, and the amount of acetone and/or butanone is at least 5.0 wt % with respect to the total amount of the solvent.

6. The precursor composition according to claim 4, wherein the solvent contains acetone and/or butanone, and the amount of acetone and/or butanone is 5.0-30 wt % with respect to the total amount of the solvent.

* * * * *